United States Patent
Eggenweiler et al.

(10) Patent No.: US 6,884,800 B1
(45) Date of Patent: Apr. 26, 2005

(54) IMIDAZOLE COMPOUNDS USED AS PHOSPHODIESTERASE VII INHIBITORS

(75) Inventors: Hans-Michael Eggenweiler, Weiterstadt (DE); Rochus Jonas, Darmstadt (DE); Michael Wolf, Darmstadt (DE); Michael Gassen, Griesheim (DE); Thomas Welge, Alsbach (DE)

(73) Assignee: Merck Patent Gesellschaft mit Beschrankter Haftung, Darmstadt (DE)

(*) Notice: Subject to any disclaimer, the term of this patent is extended or adjusted under 35 U.S.C. 154(b) by 252 days.

(21) Appl. No.: 10/129,629
(22) PCT Filed: Oct. 31, 2000
(86) PCT No.: PCT/EP00/10765
§ 371 (c)(1), (2), (4) Date: May 9, 2002
(87) PCT Pub. No.: WO01/36425
PCT Pub. Date: May 25, 2001

(30) Foreign Application Priority Data

Nov. 13, 1999 (DE) .......................................... 199 54 707

(51) Int. Cl.$^7$ ................. A61K 31/538; A61K 31/5415; C07D 413/02; C07D 417/02
(52) U.S. Cl. ............................... 514/228.5; 514/229.5; 544/60; 544/111
(58) Field of Search .......................... 514/228.5, 229.5; 544/60, 111

(56) References Cited

U.S. PATENT DOCUMENTS 2,919,271 A  12/1966  Craig et al.

FOREIGN PATENT DOCUMENTS

WO    WO 9015058 A    12/1990

Primary Examiner—Taofiq Solola
(74) Attorney, Agent, or Firm—Millen, White, Zelano & Branigan, P.C.

(57) ABSTRACT

Imidazole compounds of the formula I

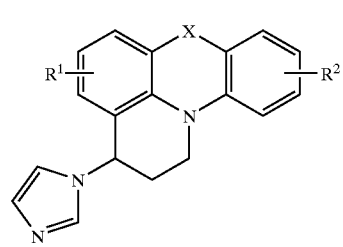

in which

R$^1$ and R$^2$, independently of one another, each denote A$^1$, OA$^1$, SA$^1$ or Hal, A$^1$ denotes H, A, alkenyl, cycloalkyl or alkylenecycloalkyl, A denotes alkyl having 1–10 carbon atoms, Hal denotes F, Cl, Br or I, and X denotes O, S, SO or SO$_2$, and their physiologically acceptable salts and/or solvates, as phosphodiesterase VII inhibitors, and their use for the preparation of a medicament.

16 Claims, No Drawings

IMIDAZOLE COMPOUNDS USED AS PHOSPHODIESTERASE VII INHIBITORS

This Application is a 371 of PCT/EP00/10765 Filed Oct. 31, 2003.

The invention relates to imidazole compounds of the formula I

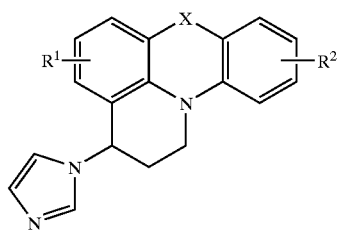

in which
R$^1$ and R$^2$, independently of one another, each denote A$^1$, OA$^1$, SA$^1$ or Hal,
A$^1$ denotes H, A, alkenyl, cycloalkyl or alkylenecycloalkyl,
A denotes alkyl having 1–10 carbon atoms,
Hal denotes F, Cl, Br or I, and
x denotes O, S, SO or SO$^2$,
and their physiologically acceptable salts and/or solvates.

Other imidazole derivatives have been described, for example, by M. Trkovnik et al. in Org. Prep. Proced. Int (1987), 19(6), 450–5, or by V. L. Savel'ev et al. In Khim.-Farm. Zh. (1983), 17(6), 697–700. Benzothiopyranoimidazole derivatives have been disclosed, for example, by V. L. Savel'ev et al. in Khim. Geterotsikl, Soedin. (1980), (4), 479–83.

The invention had the object of finding novel compounds having valuable properties, in particular those which can be used for the production of medicaments.

It has been found that the compounds of the formula I and their salts have very valuable pharmacological properties and are well tolerated. In particular, they exhibit specific inhibition of "Rolipram insensitive" cAMP phosphodiesterase (POE VII).

The biological activity of the compounds of the formula I can be determined by methods as described, for example, by M. A. Giembycz et al. in Br. J. Pharmacol. (1996), 118, 1945–1958.

The affinity of the compounds for cAMP phosphodiesterase (PDE VII) is determined by measuring their IC$_{50}$ values (concentration of the inhibitor that is required to achieve 50% inhibition of the enzyme activity). In order to carry out the determinations, homogenized SK-N-SH neuroblastoma cells were used instead of T-lymphocytes, and PDE III inhibition was carried out using Cl-930. This is a selective PDE III inhibitor (J. A. Bristol et al., J. Med. Chem. 1984, 27(9), 1099–1101). Alternatively, SK-N-SH is replaced by HUT-78 and instead of using Cl-930 inhibition is carried out with trequensin (D. Ruppert et al., Life Sci. 31:2037, 1982).

The compounds of the formula I can be employed for the treatment of asthmatic illnesses. The anti-asthmatic action can be determined, for example, analogously to the method of T. Olsson, Acta allergologica 26, 438–447 (1971).

Since cAMP inhibits osteoclastic cells and stimulates osteogenetic cells (S. Kasugai et al., M 681, and K. Miyamoto, M 682, in Abstracts of the American Society for Bone and Mineral Research, 18$^{th}$ Annual Meeting, 1996), the compounds of the formula I can be employed for the treatment of osteoporosis.

The compounds also exhibit an antagonistic action to the production of TNFα (tumour necrosis factor) and are therefore suitable for the treatment of allergic and inflammatory diseases, autoimmune diseases, such as, for example, rheumatoid arthritis, multiple sclerosis, Crohn's disease, diabetes mellitus or ulcerative colitis, transplant rejection reactions, cachexia and sepsis.

The anti-inflammatory action of the substances of the formula I and their effectiveness for the treatment of, for example, autoimmune diseases such as multiple sclerosis or rheumatoid arthritis can be determined analogously to the methods of N. Sommer et al., Nature Medicine 1, 244–248 (1995), or L. Sekut et al., Clin. Exp. Immunol. 100, 126–132 (1995).

The compounds can be employed for the treatment of cachexia. The anti-cachectic action can be tested in TNF-dependent models of cachexia (P. Costelli et al., J. Clin. Invest. 95, 2367 ff. (1995); J. M. Argiles et al., Med. Res. Rev. 17, 477 ff. (1997)).

The PDE VII inhibitors can also inhibit the growth of tumour cells and are therefore suitable for tumour therapy (for PDE IV inhibitors, cf. D. Marko et al., Cell Biochem. Biophys. 28, 75 ff. (1998)).

They can furthermore be employed for the therapy of sepsis and for the treatment of memory disorders, atherosclerosis, atopical dermatitis and AIDS, furthermore for the treatment of T cell-dependent diseases (L. Li et al., Science, 1999, 283, 848–851).

The compounds of the formula I can be employed as medicament active ingredients in human and veterinary medicine. They can furthermore be employed as intermediates for the preparation of further medicament active ingredients. In particular, the compounds of the formula I can be employed as medicament active ingredients for PDE VII inhibition in human and veterinary medicine.

The invention furthermore relates to the use of the compounds of the formula I for the preparation of a medicament for combating allergic diseases, asthma, chronic bronchitis, atopical dermatitis, psoriasis and other skin diseases, inflammatory diseases, autoimmune diseases, such as, for example, rheumatoid arthritis, multiple sclerosis, Crohn's disease, diabetes mellitus or ulcerative colitis, osteoporosis, transplant rejection reactions, cachexia, tumour growth or tumour metastases, sepsis, memory disorders, atherosclerosis and AIDS.

A denotes alkyl having 1–10 carbon atoms and has 1, 2, 3, 4, 5, 6, 7, 8, 9 or 10 carbon atoms and preferably denotes methyl, ethyl or propyl, furthermore preferably isopropyl, butyl, isobutyl, sec-butyl or tert-butyl, but also n-pentyl, neopentyl, isopentyl or hexyl. In these radicals, 1–7 H atoms may also be replaced by F and/or Cl. A therefore also denotes, for example, trifluoromethyl or pentafluoroethyl. Cycloalkyl has 3–9 carbon atoms and preferably denotes, for example, cyclopentyl or cyclohexyl. Alkenyl has 2–10 carbon atoms, is linear or branched and preferably denotes vinyl, propenyl or butenyl. Alkylenecycloalkyl has 4–10 carbon atoms and denotes, for example, methylenecyclopentyl, ethylenecyclopentyl, methylenecyclohexyl or ethylenecyclohexyl. R$^1$ and R$^2$ preferably denote, in each case independently of one another, H, fluorine, chlorine, methyl, ethyl, propyl, methoxy, ethoxy, propoxy, methylthio, cyclopentyl or cyclohexyl.

Accordingly, the invention relates, in particular, to those compounds of the formula I in which at least one of said radicals has one of the preferred meanings indicated above. Some preferred groups of compounds may be expressed by the following sub-formulae Ia to Ig, which correspond to the formula I and in which the radicals not designated in greater detail have the meaning indicated in the formula I, but in which

| | | |
|---|---|---|
| in Ia | X | denotes S; |
| in Ib | X | denotes S, |
| | $R^1$ | denotes H; |
| in Ic | X | denotes S, |
| | $R^1$ | denotes F or Cl; |
| in Id | X | denotes S, |
| | $R^2$ | denotes H; |
| in Ie | X | denotes S, |
| | $R^2$ | denotes F or Cl; |
| in If | X | denotes S, |
| | $R^1$ | denotes H, |
| | $R^2$ | denotes F or Cl; |
| in Ig | X | denotes S, |
| | $R^1$ | denotes F or Cl, |
| | $R^2$ | denotes H; |
| in Ih | X | denotes S; |
| | $A^1$ | denotes H or A, |
| | A | denotes alkyl having 1, 2, 3 or 4 carbon atoms; |
| in Ii | X | denotes S, |
| | $R^1$ and $R^2$, independently of one another, each denote $A^1$ or Hal, | |
| | $A^1$ | denotes H or A, |
| | A | denotes alkyl having 1, 2, 3 or 4 carbon atoms, |
| | Hal | denotes F or Cl; | and their physiologically acceptable salts and solvates.

The invention accordingly relates to the compounds of the formula I and to a process for the preparation of compounds of the formula I (according to claim 1 and their salts, characterized in that a compound of the formula II

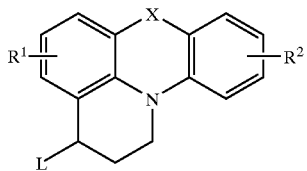

in which
$R^1$, $R^2$ and X are as defined above,
and L denotes Cl, Br, OH, $SCH_3$ or a reactive esterified OH group, is reacted with imidazole,
and/or a compound of the formula I is converted into one of its salts.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for said reactions. Use can also be made here of variants which are known per se, but are not mentioned in greater detail here.

In the compounds of the formula II, $R^1$, $R^2$ and X have the meanings indicated, in particular have the preferred meanings indicated.

If L denotes a reactive esterified OH group, this is preferably alkylsulfonyloxy having 1–6 carbon atoms (preferably methylsulfonyloxy) or arylsulfonyloxy having 6–10 carbon atoms (preferably phenyl- or p-tolylsulfonyloxy, furthermore also 2-naphthalenesulfonyloxy).

The starting compounds of the formula II are generally known. If they are not known, they can be prepared by methods known per se.

Compounds of the formula II can be prepared by methods known from the literature, for example by reduction of the corresponding carbonyl precursor using a complex metal hydride.

In detail, the reaction of the compounds of the formula II with imidazole is carried out in the presence or absence of an inert solvent at temperatures between about –20 and about 150°, preferably between 20 and 100°.

The addition of an acid-binding agent, for example an alkali or alkaline earth metal hydroxide, carbonate or bicarbonate or another salt of a weak acid of the alkali or alkaline earth metals, preferably of potassium, sodium or calcium, or the addition of an organic base, such as triethylamine, dimethylamine, pyridine or quinoline, may be favourable.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide, N-methylpyrrolidone or dimethylformamide (DMF); nitriles, such as acetonitrile; sulfoxides, such as dimethyl sulfoxide (DMSO); nitro compounds, such as nitromethane or nitrobenzene; esters, such as ethyl acetate, or mixtures of the said solvents.

A base of the formula I can be converted into the associated acid-addition salt using an acid, for example by reaction of equivalent amounts of the base and the acid in a suitable solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as ortho-phosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethane-sulfonic acid, benzenesulfonic acid, p-toluenesulfonic acid, naphthalene-mono- and -disulfonic acids, laurylsulfuric acid. Salts with physiologically unacceptable acids, for example picrates, can be used for the isolation and/or purification of the compounds of the formula I.

The invention also relates to medicaments of the formula I and their physiologically acceptable salts as phosphodiesterase VII inhibitors.

The invention furthermore relates to pharmaceutical preparations comprising at least one phosphodiesterase VII inhibitor of the formula I and/or one of its physiologically acceptable salts and/or solvates for combating allergic diseases, asthma, chronic bronchitis, atopical dermatitis, psoriasis and other skin diseases, inflammatory diseases, autoimmune diseases, such as, for example, rheumatoid arthritis, multiple sclerosis, Crohn's disease, diabetes mellitus or ulcerative colitis, osteoporosis, transplant rejection reactions, cachexia, tumour growth or tumour metastases, sepsis, memory disorders, atherosclerosis and AIDS.

The substances here are generally preferably administered in doses of between about 1 and 500 mg, in particular between 5 and 100 mg, per dosage unit. The daily dose is preferably between about 0.02 and 10 mg/kg of body weight. However, the specific dose for each patient depends on a wide variety of factors, for example on the efficacy of the specific compound employed, on the age, body weight, general state of health, sex, on the diet, on the time and method of administration, on the rate of excretion, medicament combination and severity of the particular disease to which the therapy applies. Oral administration is preferred.

The pharmaceutical preparations can be used as medicaments in human or veterinary medicine. Suitable excipients are organic or inorganic substances which are suitable for enteral (for example oral), parenteral or topical administration and with which the novel compounds do not react, for example water, vegetable oils, benzyl alcohols, alkylene glycols, poly-ethylene glycols, glycerol triacetate, gelatine, carbohydrates, such as lactose or starch, magnesium stearate, talc, Vaseline. Suitable for oral administration are, in particular, tablets, pills, coated tablets, capsules, powders, granules, syrups, juices or drops, suitable for rectal administration are suppositories, suitable for parenteral administration are solutions, preferably oily or aqueous solutions, furthermore suspensions, emulsions or implants, and suitable for topical application are ointments, creams or powders. The novel compounds may also be lyophilized and the resultant lyophilizates used, for example, for the preparation of injection preparations. The preparations indicated may be sterilized and/or comprise auxiliaries, such as lubricants, preservatives, stabilizers and/or wetting agents, emulsifiers, salts for modifying the osmotic pressure, buffer sub-stances, dyes, flavours and/or a plurality of further active ingredients, for example one or more vitamins.

The invention relates, in particular, to the compounds of the formula I listed in the examples below and their physiologically acceptable salts and/or solvates as PDE VII inhibitors and to their use for the preparation of a medicament for combating allergic diseases, asthma, chronic bronchitis, atopical dermatitis, psoriasis and other skin diseases, inflammatory diseases, autoimmune diseases, such as, for example, rheumatoid arthritis, multiple sclerosis, Crohn's disease, diabetes mellitus or ulcerative colitis, osteoporosis, transplant rejection reactions, cachexia, tumour growth or tumour metastases, sepsis, memory disorders, atherosclerosis and AIDS.

EXAMPLES

10-Chloro-3-imidazol-1-yl-2,3-dihydro-1H-pyrido[3,2,1-kl]phenothiazine,
4chloro-3-imidazol-1-yl-2,3-dihydro-1H-pyrido[3,2,1-kl]phenothiazine,
10-methoxy-3-imidazol-1-yl-2,3-dihydro-1H-pyrido[3,2,1-kl]phenothiazine,
10-propoxy-3-imidazol-1-yl-2,3-dihydro-1H-pyrido[3,2,1-kl]phenothiazine,
10-methylthio-3-imidazol-1-yl-2,3-dihydro-1H-pyrido[3,2,1-kl]phenothiazihe,
10-fluoro-3-imidazol-1-yl-2,3-dihydro-1H-pyrido[3,2,1-kl]phenothiazine,
4,10-dichloro-3-imidazol-1-yl-2,3-dihydro-1H-pyrido[3,2,1-kl]phenothiazine,
10-trifluoromethyl-3-imidazol-1-yl-2,3-dihydro-1H-pyrido[3,2,1-kl]pheno-thiazine,
4-cyclopentoxy-3-imidazol-1-yl-2,3-dihydro-1H-pyrido[3,2,1-kl]pheno-thiazine,
10-chloro-3-imidazol-1-yl-2,3-dihydro-1H-7-oxa-11b-azabenzo[de]-anthracene,
10-chloro-3-imidazol-1-yl-2,3-dihydro-1H-pyrido[3,2,1-kl]phenothiazine 7,7-dioxide.

Preparation Example

The compounds of the formula I are prepared analogously to the following reaction scheme:

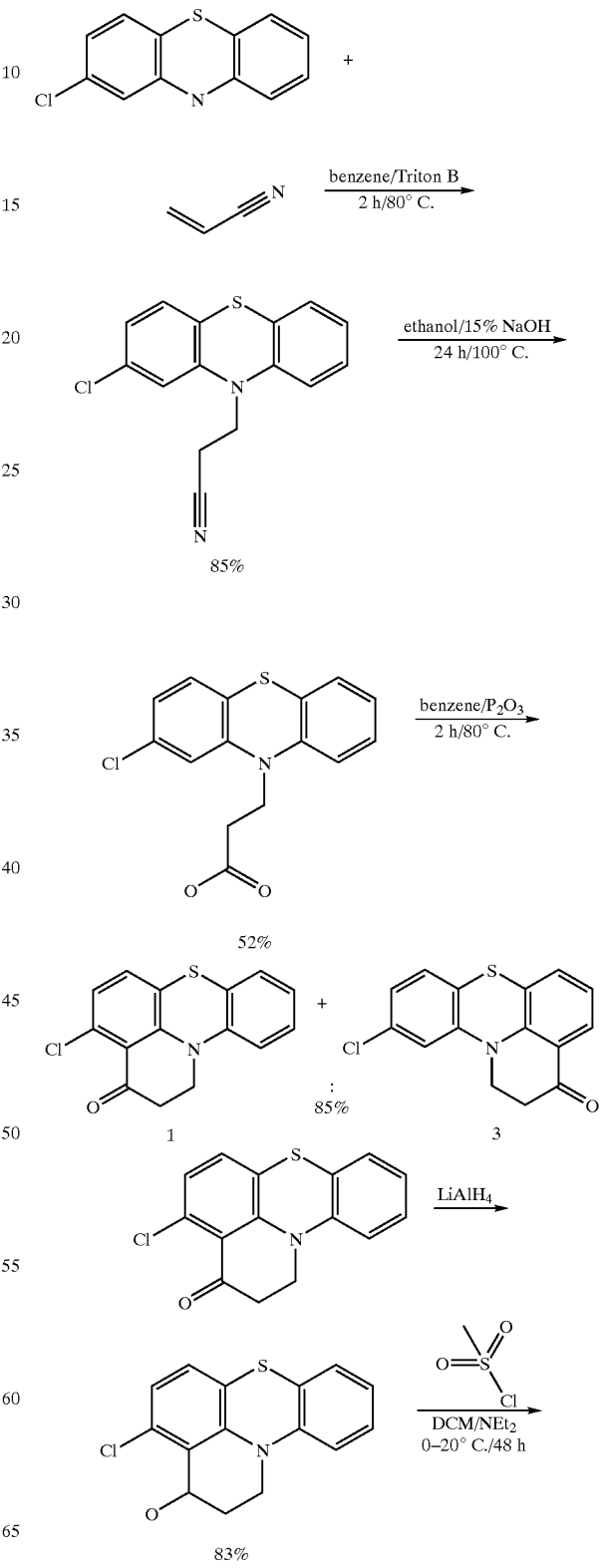

The examples below relate to pharmaceutical preparations:

Example A
Injection Vials

A solution of 100 g of a phosphodiesterase VII inhibitor of the formula I and 5 g of disodium hydrogenphosphate in 3 I of bidistilled water is adjusted to pH 6.5 using 2N hydrochloric acid, sterile filtered, transferred into injection vials, lyophilized under sterile conditions and sealed under sterile conditions. Each injection vial contains 5 mg of active ingredient.

Example B
Suppositories

A mixture of 20 g of a phosphodiesterase VII inhibitor of the formula I is melted with 100 g of soya lecithin and 1400 g of cocoa butter, poured into moulds and allowed to cool. Each suppository contains 20 mg of active ingredient.

Example C
Solution

A solution is prepared from 1 g of a phosphodiesterase VII inhibitor of the formula I, 9.38 g of $NaH_2PO_4 \cdot 2H_2O$; 28.48 g of $Na_2HPO_4 \cdot 12 H_2O$ and 0.1 g of benzalkonium chloride in 940 ml of bidistilled water. The pH is adjusted to 6.8, and the solution is made up to 1 I and sterilized by irradiation. This solution can be used in the form of eye drops.

Example D
Ointment 500 mg of a phosphodiesterase VII inhibitor of the formula I are mixed with 99.5 g of Vaseline under aseptic conditions.

Example E
Tablets

A mixture of 1 kg of phosphodiesterase VII inhibitor of the formula I, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

Example F
Coated Tablets

Tablets are pressed analogously to Example E and subsequently coated in a conventional manner with a coating of sucrose, potato starch, talc, tragacanth and dye.

Example G
Capsules 2 kg of phosphodiesterase VII inhibitor of the formula I are introduced into hard gelatine capsules in a conventional manner in such a way that each capsule contains 20 mg of the active ingredient.

Example H
Ampoules

A solution of 1 kg of phosphodiesterase VII inhibitor of the formula I in 60 I of bidistilled water is sterile filtered, transferred into ampoules, lyophilized under sterile conditions and sealed under sterile conditions. Each ampoule contains 10 mg of active ingredient.

Example I
Inhalation Spray 14 9 of phosphodiesterase VII inhibitor of the formula I are dissolved in 10 I of isotonic NaCl solution, and the solution is transferred into commercially available spray containers with a pump mechanism. The solution can be sprayed into the mouth or nose. One spray shot (about 0.1 ml) corresponds to a dose of about 0.14 mg.

What is claimed is:
1. An imidazole compound of formula I.

in which $R^1$ and $R^2$, independently of one another, each denote $A^1$, $OA^1$, $SA^1$ or Hal, $A^1$ denotes H, A, alkenyl, cycloalkyl or alkylenecycloalkyl, A denotes alkyl having 1–10 carbon atoms, Hal denotes F, Cl, Br or I, and X denotes O, S, SO or $SO_2$, a physiologically acceptable salt or solvate thereof.

2. A pharmaceutical composition comprising an imidazole compound of formula I according to claim 1 or a physiologically acceptable salt or solvate thereof and a physiologically acceptable carrier.

3. A method for the inhibition of phosphodiesterase VII, comprising administering a compound of claim 1 to a host in need thereof.

4. A method for treating an allergic disease, asthma, chronic bronchitis, atopical dermatitis, psoriasis, a skin disease, an inflammatory disease, an autoimmune disease, rheumatoid arthritis, multiple sclerosis, Crohn's disease, diabetes mellitus, ulcerative colitis, osteoporosis, transplant rejection reactions, cachexia, tumour growth, tumour metastases, sepsis, a memory disorder, atherosclerosis or AIDS, comprising administering a compound of claim 1 to a host in need thereof.

5. A method for treating an allergic disease, asthma, chronic bronchitis, atopical dermatitis, psoriasis, an inflammatory disease, rheumatoid arthritis, multiple sclerosis, Crohn's disease, diabetes mellitus, ulcerative colitis, osteoporosis, transplant rejection reactions, cachexia, sepsis, or, atherosclerosis, comprising administering a compound of claim 1 to a host in need thereof.

6. A process for the preparation of a compound of formula I according to claim 1, comprising reacting a compound of formula II

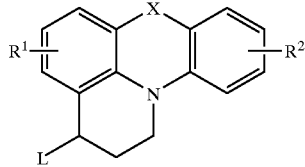

II in which

R$^1$, R$^2$ and X are as defined above, and L denotes Cl, Br, OH, SCH$_3$ or a reactive esterified OH group, with imidazole, and optionally converting a compound of formula I into a salt thereof.

7. A compound according to claim 1, wherein X is S.

8. A compound according to claim 1, wherein X is S and R$^1$ is H.

9. A compound according to claim 1, wherein X is S and R$^1$ is F or Cl.

10. A compound according to claim 1, wherein X is S and R$^2$ is H.

11. A compound according to claim 1, wherein X is S and R$^2$ is F or Cl.

12. A compound according to claim 1, wherein X is S and R$^1$ is H and R$^2$ is F or Cl.

13. A compound according to claim 1, wherein X is S and R$^1$ is F or Cl and R$^2$ is H.

14. A compound according to claim 1, wherein X is S and A$^1$ is H or A and A is C$_{1-4}$ alkyl.

15. A compound according to claim 1, wherein X is S, R$^1$ and R$^2$ are each independently A$^1$ or Hal, A$^1$ is H or A, A is C$_{1-4}$ alkyl and Hal is F or Cl.

16. A method for treating an allergic disease, asthma, chronic bronchitis, atopical dermatitis, psoriasis, rheumatoid arthritis, Crohn's disease, diabetes mellitus, ulcerative colitis, cachexia, sepsis, or atherosclerosis, comprising administering a compound of claim 1 to a host in need thereof.

* * * * *